United States Patent
Cox et al.

(10) Patent No.: US 10,279,078 B2
(45) Date of Patent: May 7, 2019

(54) CROSSLINKABLE 3D PRINTED BIOMATERIAL-BASED IMPLANTS AND METHODS OF MANUFACTURE THEREOF

(71) Applicants: Daniel Cox, Belgrade, MT (US); Dominic Denty, Idaho Falls, ID (US); Helena Lovick, Belgrade, MT (US)

(72) Inventors: Daniel Cox, Belgrade, MT (US); Dominic Denty, Idaho Falls, ID (US); Helena Lovick, Belgrade, MT (US)

(73) Assignee: Bacterin International, Inc., Belgrade, MT (US)

( * ) Notice: Subject to any disclaimer, the term of this patent is extended or adjusted under 35 U.S.C. 154(b) by 0 days.

(21) Appl. No.: 14/986,012

(22) Filed: Dec. 31, 2015

(65) Prior Publication Data

US 2016/0184480 A1  Jun. 30, 2016

Related U.S. Application Data

(60) Provisional application No. 62/098,933, filed on Dec. 31, 2014.

(51) Int. Cl.
| | |
|---|---|
| *A61L 27/36* | (2006.01) |
| *A61L 27/54* | (2006.01) |
| *A61L 27/58* | (2006.01) |
| *B33Y 70/00* | (2015.01) |
| *B29C 64/106* | (2017.01) |
| *B29K 105/00* | (2006.01) |

(Continued)

(52) U.S. Cl.
CPC ....... *A61L 27/3691* (2013.01); *A61L 27/3604* (2013.01); *A61L 27/365* (2013.01); *A61L 27/3608* (2013.01); *A61L 27/54* (2013.01); *A61L 27/58* (2013.01); *B29C 64/106* (2017.08); *B33Y 70/00* (2014.12); *A61L 2300/404* (2013.01); *A61L 2300/406* (2013.01); *A61L 2300/414* (2013.01); *A61L 2300/43* (2013.01); *A61L 2300/64* (2013.01); *A61L 2430/02* (2013.01); *B29K 2105/0058* (2013.01); *B29K 2995/006* (2013.01); *B29K 2995/0056* (2013.01); *B29L 2031/7532* (2013.01); *B33Y 10/00* (2014.12); *B33Y 80/00* (2014.12)

(58) Field of Classification Search
None
See application file for complete search history.

(56) References Cited

U.S. PATENT DOCUMENTS

| | | | |
|---|---|---|---|
| 5,314,476 A | 5/1994 | Prewett et al. | |
| 5,518,680 A * | 5/1996 | Cima ............... | A61F 2/022 264/401 |

(Continued)

OTHER PUBLICATIONS

Edwards et al., Osteoinduction of Human Demineralized Bone: Characterization in a Rat Model, Clinical Orthopedics and Related Research, 1998, vol. 357, pp. 219-228, 1 page, abstract only.

(Continued)

*Primary Examiner* — Brian Gulledge
(74) *Attorney, Agent, or Firm* — Sheridan Ross P.C.

(57) ABSTRACT

The invention provides articles of 3D printed biomaterials with retained physical properties and biological activity and methods of using the articles. Furthermore, the invention provides manufacturing conditions to generate 3D printed biomaterials with highly preserved biological activity.

23 Claims, 2 Drawing Sheets

(51) Int. Cl.
   *B29L 31/00*   (2006.01)
   *B33Y 10/00*   (2015.01)
   *B33Y 80/00*   (2015.01)

(56) References Cited

U.S. PATENT DOCUMENTS

| | | |
|---|---|---|
| 6,530,958 B1 | 3/2003 | Cima et al. |
| 7,747,305 B2 | 6/2010 | Dean et al. |
| 8,843,229 B2 | 9/2014 | Vanasse et al. |
| 2006/0193885 A1* | 8/2006 | Leonard Neethling ........................ A61L 27/3687 424/422 |
| 2009/0155378 A1* | 6/2009 | Behnam .............. A61L 27/3608 424/549 |
| 2011/0054613 A1* | 3/2011 | Hansen .............. A61B 17/7064 623/17.11 |

OTHER PUBLICATIONS

Ohta et al., "The effects of heat on the biological activity of recombinant human bone morphogenetic protein-2," Journal of Bone and Mineral Metabolism, 2005, vol. 23(6), pp. 420-425, 2 pages, abstract only.

Wang et al., "Synthesis and characterizations of biodegradable and crosslinkable poly(ε-caprolactone fumarate), poly(ethylene glycol) fumarate), and their amphiphilic copolymer," Biomaterials, 2006, vol. 27(6), pp. 832-841, 1 page, abstract only.

\* cited by examiner

US 10,279,078 B2

CROSSLINKABLE 3D PRINTED BIOMATERIAL-BASED IMPLANTS AND METHODS OF MANUFACTURE THEREOF

CROSS REFERENCE TO RELATED APPLICATIONS

This application claims priority under 35 U.S.C. § 119(e) to U.S. Provisional Patent Application Ser. No. 62/098,933 filed Dec. 31, 2014, which is incorporated herein in its entirety by reference.

FIELD OF THE INVENTION

The present embodiments generally relate to crosslinkable three-dimensional (3D) printed biomaterial-based implants and methods for the 3D printing manufacture thereof.

BACKGROUND

Methods for 3D printing manufacture of products are known in the prior art. The use of biomaterials such as allograft tissue in 3D printers is limited by factors such as curing temperatures and the form of the raw material input. U.S. Pat. No. 6,530,958 entitled "Tissue Regeneration Matrices By Solid Free-Form Fabrication Techniques" (which is incorporated by reference in its entirety) discloses methods for formulated devices for tissue regeneration using computer-aided design in combination with solid free-form fabrication technology. U.S. Pat. No. 8,843,229 entitled "Metallic Structures Having Porous Regions From Imaged Bone At Pre-Defined Anatomic Locations" (which is incorporated by reference in its entirety) discloses metallic structures with porous regions to represent the architecture of bone. Methods for imaging bone at pre-defined anatomic locations to create the implants are also disclosed. U.S. Pat. No. 7,747,305 entitled "Computer-Aided Design Of Skeletal Implants" (which is incorporated by reference in its entirety) discloses methods for production of an implant for a patient prior to an operation.

A need remains for a facile method of generating biomaterial-based products with retained biological activity and retained physical properties for subsequent patient implantation.

SUMMARY OF THE INVENTION

The invention comprises articles of 3D printed biomaterials with retained physical properties and biological activity. Furthermore, the invention provides manufacturing conditions to generate 3D printed biomaterials with highly preserved biological activity. Suitable uses of the invention are also provided.

The disclosed invention is directed to methods of manufacturing biomaterial-based implants via a crosslinking 3D printing step. The biomaterial-based implants comprise a form of selected dimensions. The properties of the biomaterial-based implants include biocompatibility, a surface for cellular infiltration, interconnected porosity, and access to an infinite variety of shapes and sizes. Additionally the use of easily crosslinkable additives mixed with the biomaterial allows for 3D printing of the biomaterial with mild conditions for "curing" or "hardening" the final article. The use of a mild curing step, instead of traditional thermal curing processes, limits or eliminates degradation of the inherent physical properties and biological activity of the biomaterial. The methods of manufacturing rely on judicious selection of biomaterial and crosslinkable materials. In preferred embodiments, the biomaterial-based implants are suitable for implantation into a patient.

An aspect of the invention is a biomaterial-based implant. The implant can be formed under a mild crosslinking condition. The mild crosslinking condition is selected from the group consisting of visible light exposure, ultraviolet exposure and combinations thereof. At least one pre-implantation property selected from the group consisting of cohesion, shape, or size of the biomaterial-based implants is within between about 60% to about 100% of the at least one preimplantation property up to about five years following formation of the implant. The biomaterial-based implant retains greater than about 80% of at least one biological activity selected from the group consisting of osteoconductivity, osteoinductivity, chondroinductivity, cellular recruitment, and cell differentiation.

An aspect of the invention is a method of generating a three-dimensional biomaterial-based implant. The method includes providing at least one biomaterial and at least one crosslinkable material to a 3D printer. The biomaterial and crosslinkable material are crosslinked during 3D printing to form the three-dimensional biomaterial-based implant. The crosslinking occurs under a mild crosslinking condition is selected from the group consisting of light exposure, radiation, oxidation and combinations thereof.

An aspect of the invention is a method of 3D printing a biomaterial-based implant. The method includes combining a biomaterial and a suitable crosslinking agent using a 3D printer to create an implant of desired dimensions.

DETAILED DESCRIPTION OF THE INVENTION

Figure 1:
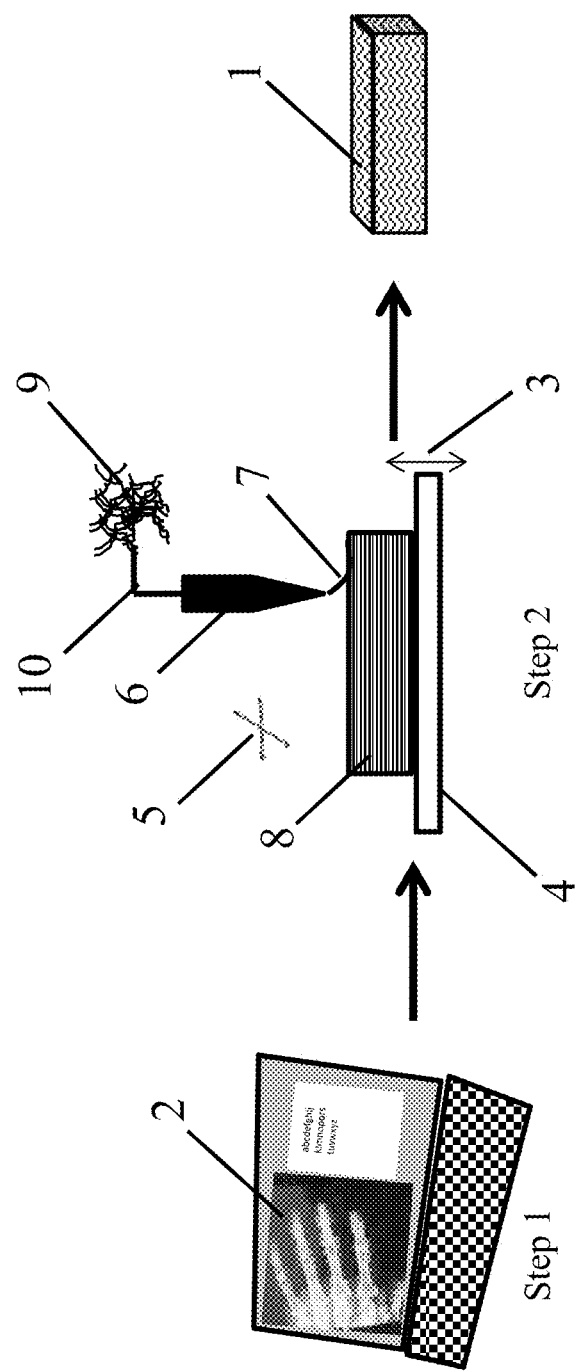
FIG. 1 illustrates a method to form biomaterial-based implants via a 3D printing of the implants in accordance with preferred embodiments of the present invention.

The present invention relates to 3D-printed biomaterial-based implants and methods of making the same.

"3D printing technology," as used herein, refers to a variety of additive manufacturing processes for making a three-dimensional object based on a 3D model or electronic source input under computer control.

"Allogeneic" or "allograft," as used herein, refers to tissue derived from a non-identical donor of the same species.

"Autogeneic" or "autograft," as used herein, refers to tissue derived from and implanted into the same identical patient.

"Biocompatible," as used herein, refers to the property of being biologically compatible with a living being by not causing harm.

"Biodegradable," as used herein, refers to matter capable of being broken down by biological or environmental processes.

"Biological activity," as used herein, refers to the natural, beneficial effects of the biological tissue within the final biomaterial-based implants of the invention. For example, biological activity of bone materials refers to the inherent osteoconductivity, osteoinductivity, chondroinductivity, cellular recruitment, cell differentiation and combinations thereof.

"Biomaterial," as used herein, includes plant or animal derived tissues. In preferred embodiments, the biomaterial is animal derived cortical bone, cancellous bone, connective tissue, tendon, pericardium, dermis, cornea, dura matter, fascia, heart valve, ligament, capsular graft, cartilage, collagen, nerve, placental tissue, and combinations thereof. In some embodiments, the biomaterial-based implants are formed from demineralized bone matrix (DBM) material.

"Crosslinkable," as used herein, refers to the ability of a material to be further bonded together by covalent or ionic bonds.

"Mild Crosslinking Conditions," as used herein, refers to 3D printing conditions where a crosslinkable material mixed with a biomaterial is cured in a manner which limits or eliminates degradation of the inherent physical properties and biological activity of the biomaterial.

"Osteoconductive," as used herein, refers to the ability of a material to induce bone healing by providing a scaffold for new bone growth.

"Osteoinductive," as used herein, refers to the ability of a material to induce bone healing via recruitment of osteoprogenitor cells.

"Patient," as used herein, refers to a living recipient of the biomaterial-based implants of the present invention.

"Physical Integrity," as used herein, refers to retained cohesion, shape, and size of the biomaterial-based implants pre-implantation and at a point prior to or at the time of implantation. For example, in some embodiments at the time of implantation, the biomaterial-based implants can retain between about 60% to about 100% of the original printed volume, or can retain between about 60% to about 100% of at least two the original dimensions, or can retain between about 60% to about 100% of the original implant compression strength, or can retain between about 60% to about 100% of the original implant's flexural strength. In some embodiments, the biomaterial-based implants can retain between about 60% to about 100% of the original printed volume, or can retain between about 60% to about 100% of at least two the original dimensions, or can retain between about 60% to about 100% of the original implant compression strength, or can retain between about 60% to about 100% of the original implant's flexural strength for up to about one month, two months, three months, six months, one year, two years, three years, or five years after the formation of the implant.

"Xenogeneic" or "xenograft," as used herein, is defined as tissue derived from a non-identical donor of a different species.

The biomaterial-based implants of the invention can be used as scaffolding for tissue ingrowth following implantation into a patient. The biomaterial-based implants of the invention can be used to provide structural support following implantation into a patient. Furthermore, while the invention can be used to produce a biomaterial-based sheet that can be cut to form a specific shape, the invention allows the biomaterial-based implants to be formed without this additional cutting step.

The biomaterial-based implants of the invention have many advantages over the prior art. The process of combining easily crosslinkable material with a biomaterial allows the biomaterial to be 3D printed while preserving the physical integrity and biological activity of the biomaterial.

The biomaterial can be allogeneic, autogeneic, or xenogeneic. The biomaterial is selected from the group consisting of bone, connective tissue, tendon, pericardium, dermis, cornea, dura matter, fascia, heart valve, ligament, capsular graft, cartilage, collagen, nerve, placental tissue, and combinations thereof. In some embodiments, the biomaterial may be bone. When the implants are bone-derived, the bone can be cortical, cancellous, or a combination of the two bone types. The bone for the invention can be generated by a variety of methods and techniques known in the prior art, for example U.S. Pat. No. 5,314,476 ("the '476 patent"), which is incorporated in its entirety by reference. The bone comprising the biomaterial-based implant can be mineralized, fully demineralized, partially demineralized, surface demineralized, or a combination of the foregoing. Demineralized bone matrix (DBM) for use by the disclosed method can be prepared using any method or techniques known in the art, for a typical demineralization protocol, for example the method discussed in the '476 patent.

An aspect of the invention is a biomaterial-based implant formed under mild crosslinking conditions with retained physical integrity and maximally preserved biological activity. The physical integrity of at least one of cohesion, shape, and size of the biomaterial-based implants when compared pre- and post-implantation. The biological activity that is preserved is at least one of osteoconductivity, osteoinductivity, chondroinductivity, cellular recruitment, and cell differentiation. The biological activity is at least about 80% of the biological activity of a natural bone body, cartilage body, or applicable biomaterial body source. Furthermore, the biological activity can include the activity of native and intrinsic growth factors within the bone matter to promote osteoinductivity of the resultant biomaterial-based implant. Native and intrinsic growth factors that can be maximally preserved within the biomaterial-based implant include, but are not limited to, calcium regulating hormones, parathyroid hormone (PHT), transforming growth factor beta (TGF-beta), prostaglandin E2 (PGE2), bone morphogenetic proteins (BMPs, e.g., BMP-2), and insulin like growth factors (IGFs, e.g., IGF-1). The mild crosslinking conditions can include visible light exposure or ultraviolet light exposure or combinations thereof. Other mild crosslinking conditions can include ozone oxidation, air oxidation, oxygen-rich atmosphere exposure, and oxidation by exposure to other oxidizing gases.

In some embodiments, the biomaterial-based implant can range in thickness from about 0.1 mm to 100 mm, from about 0.3 mm to 50 mm, from about 0.5 to 30 mm. The biomaterial-based implant can range in length from about 5 mm to 500 cm, from about 10 mm to 200 cm, from about 10 mm to 100 cm. The biomaterial-based implant can range in width from about 5 mm to 50 cm, from about 10 mm to 20 cm, from about 10 mm to 10 cm. Each layer of the 3D biomaterial-based implant can range from about 0.01 mm to about 1.0 mm. In some embodiments, between about 1 to about 50,000 layers of the biomaterial can be layered to produce the 3D biomaterial-based implant. At least one dimension can be determined by at least one dimension of an implantation site.

The biomaterial of the implant can be selected from the group consisting of a bone, a connective tissue, a tendon, a pericardium, a dermis, a cornea, a dura matter, a fascia, a heart valve, a ligament, a capsular graft, a cartilage, a collagen, a nerve, a placental tissue, and combinations thereof. When the biomaterial is bone, the bone can be cortical bone, cancellous bone, corticocancellous bone, or combinations thereof. The bone can be demineralized, partially demineralized, fully mineralized, or combinations thereof. In some embodiments, the biomaterial-based implants can be formed from DBM with a residual calcium level of less than or equal to about 8%, about 6%, about 4%, or about 2%. In some embodiments, the residual calcium level can be about 0%.

The biomaterial can be combined with a crosslinkable material, an additive, a binder, a solvent, or combinations thereof. Suitable crosslinkable materials include, but are not limited to, a biodegradable polymer, a biocompatible polymer, and combinations thereof. The polymers or copolymers which can be used for this invention specifically relate to biodegradable polymers. Biodegradable polymers or copolymers which can be used for this invention include, but are not limited to, polycaprolactones, polyethylene glycols, polyhydroxyalkanoates, polyesteramides, polylactides, polyglycolides, poly(lactide-co-glycolide)s, polyorthoesters, polyoxazolines, and polyurethanes. These polymers can be used alone or in combination with one another. In preferred embodiments, the polymers can be derivatized to include the addition of a crosslinkable functional group. The addition of the crosslinkable functional group to the polymers can be performed using any method or techniques known in the art, for example the methods reported in Wang, S. et al., Biomaterials, 27, pp. 832-841 (2006), which is incorporated in its entirety by reference. Biodegradable polymers can gradually release at least one additive from the biomaterial-based implant following implantation. The release rate can be between about 1 ng/hr to about 1 g/hr.

The 3D printable mixtures of the invention can include other components in addition to the biomaterial and crosslinkable material. Suitable additives include, but are not limited to, bioactive agents, biocompatible minerals, and combinations thereof. Between about 0 wt. % to about 50 wt. % of the additive in the total weight of the biomaterial can be used. Bioactive agents including, but not limited to, antibiotics, anti-infective agent(s) such as silver sulfadiazine, chlorhexidine, gentamicin, tobramycin, or vancomycin, or combinations thereof. The biomaterial and/or crosslinkable material can also be combined with hormones, growth factors, cells, or combinations thereof. Suitable hormones and growth factors that can be combined with the biomaterial and/or crosslinkable material include, but are not limited to, calcium regulating hormones, PHT, TGF-beta, PGE2, BMPs, IGFs and combinations thereof. Suitable cell types that can be combined with the biomaterial and/or crosslinkable material include, but are not limited to, blood cells, mesenchymal stem cells, chondroblasts, osteoblasts, and combinations thereof. Between about 0 wt. % to about 50 wt. % of hormones, growth factors, or cells can be added to the total weight of the biomaterial and/or crosslinkable material. Additionally, the biomaterial and/or crosslinkable material can be combined with biocompatible minerals including, but not limited to, bioactive glasses, calcium phosphate, calcium sulfate, hydroxyapatite, or combinations of biocompatible materials. Between about 0 wt. % to about 50 wt. % of the biocompatible minerals in the total weight of the biomaterial and/or crosslinkable material can be used.

Binding agents can include polymers, glues, gums, sugars, cellulose ethers, resins, similar materials and combinations thereof. Between about 0 wt. % to about 75 wt. % of the binding agent to the total weight of the mixture can be used with the biomaterial. Solvents can be combined with the biomaterial in the presence or absence of the binding agents to facilitate 3D printing. Between about 0 vol. % to about 90 vol. % of the solvent can be used in the total mixture. The viscosity of the mixture at about 25° C. after the solvent is added can be between about 0.70 mPa-s to about 1000 mPa-s. The solvents can include water, alcohols, biocompatible organic solvents, buffers, similar materials and combinations thereof. Suitable biocompatible organic solvents include, but are not limited to, acetonitrile, dimethyl sulfoxide, acetone, ethyl acetate and combinations thereof. Suitable alcohols include, but are not limited to, ethanol, isopropanol, methanol and combinations thereof. Suitable buffers include, but are not limited to, Hank's balanced salt solution, phosphate buffered saline, saline and combinations thereof.

An aspect of the invention is a method of generating a three-dimensional biomaterial-based implant. The method includes providing at least one biomaterial and a crosslinkable material to a 3D printer. The biomaterial and crosslinkable material can be crosslinked during 3D printing to form the three-dimensional biomaterial-based implant.

The biomaterial and crosslinkable material can be mixed prior to providing the mixture to the 3D printer. About 1 wt. % and about 30 wt. % of the biomaterial and between about 70 wt. % to about 99 wt. % of the crosslinkable material can be provided to generate the implant.

The biomaterial can be a powder, a fiber, a particle, a bead, a microsphere, a pebble, a pellet, a block, and combinations thereof for use in 3D printer applications. The at least one dimension of the biomaterial must be smaller than the diameter of the opening on the extrusion head on the printer so that the material can pass through the opening of the extrusion head. The biomaterials used for forming the biomaterial-based implants can be of lengths of about 0.01 mm to about 200 mm, of about 0.1 mm to about 150 mm, of about 1 mm to about 70 mm, to about 5 mm to about 60 mm. The biomaterials may have diameters of about 0.01 mm to about 30 mm, of about 0.2 mm to about 15 mm, of about 0.5 mm to about 10 mm, to about 1 mm to about 8 mm.

The printer can produce an implant where at least one dimension is determined by at least one dimension of an implantation site.

The functional groups within the crosslinkable material can be crosslinked under mild conditions via oxidation, radiation, or other chemical means. In some embodiments, the crosslinker can be crosslinked by exposure to atmospheric oxygen, an oxygen-rich atmosphere, or a combination of oxidative gases for between 1 millisecond to about 10 minutes per layer of 3D printing, at a pressure between about 0.1 atm to about 10 atm, and a temperature of between about 10° C. to about 50° C. In some embodiments, the material can be crosslinked by exposure to visible light (light with a wavelength of about 400 nm to about 700 nm) or UV light (light with a wavelength of about 400 nm to about 10 nm). For example, the crosslinkable material can form stable crosslinkages after exposure to visible or UV light for a duration of between about 1 millisecond to about 1 minute per layer of 3D printing.

The implant can retain biological activity. Biological activity that can be preserved includes, but is not limited to, at least one of osteoconductivity, osteoinductivity, chondroinductivity, cellular recruitment, and cell differentiation. The biological activity is at least about 80% of the biological activity of a natural bone body, cartilage body, or applicable biomaterial body source. Furthermore, the biological activity can include the activity of native and intrinsic growth factors within the bone matter to promote osteoinductivity of the resultant biomaterial-based implant. Native and intrinsic growth factors that can be maximally preserved within the biomaterial-based implant include, but are not limited to, calcium regulating hormones, PHT, TGF-beta, PGE2, BMPs, and IGFs. The mild crosslinking conditions can include visible light exposure or ultraviolet light exposure or combinations thereof. Other mild crosslinking conditions can include ozone oxidation, air oxidation, oxygen-rich atmosphere exposure, and oxidation by exposure to other oxidizing gases.

In some embodiments, the implant can range in thickness from about 0.1 mm to 100 mm, from about 0.3 mm to 50 mm, from about 0.5 to 30 mm. The biomaterial-based implant can range in length from about 5 mm to 500 cm, from about 10 mm to 200 cm, from about 10 mm to 100 cm. The biomaterial-based implant can range in width from about 5 mm to 50 cm, from about 10 mm to 20 cm, from about 10 mm to 10 cm. Each layer of the 3D biomaterial-based implant can range from about 0.01 mm to about 1.0 mm. In some embodiments, between about 1 to about 50,000 layers of the biomaterial can be layered to produce the 3D biomaterial-based implant. At least one dimension can be determined by at least one dimension of an implantation site.

The biomaterial of the implant can be selected from the group consisting of a bone, a connective tissue, a tendon, a pericardium, a dermis, a cornea, a dura matter, a fascia, a heart valve, a ligament, a capsular graft, a cartilage, a collagen, a nerve, a placental tissue, and combinations thereof. When the biomaterial is bone, the bone can be cortical bone, cancellous bone, corticocancellous bone, or combinations thereof. The bone can be demineralized, partially demineralized, fully mineralized, or combinations thereof. In some embodiments, the biomaterial-based implants can be formed from DBM with a residual calcium level of less than or equal to about 8%, about 6%, about 4%, or about 2%. In some embodiments, the residual calcium level can be about 0%.

The biomaterial can be combined with a crosslinkable material, an additive, a binder, a solvent, or combinations thereof. Suitable crosslinkable materials include, but are not limited to, a biodegradable polymer, a biocompatible polymer, and combinations thereof. The polymers or copolymers which can be used for this invention specifically relate to biodegradable polymers. Biodegradable polymers or copolymers which can be used for this invention include, but are not limited to, polycaprolactones, polyethylene glycols, polyhydroxyalkanoates, polyesteramides, polylactides, polyglycolides, poly(lactide-co-glycolide)s, polyorthoesters, polyoxazolines, and polyurethanes. These polymers can be used alone or in combination with one another. In preferred embodiments, the polymers can be derivatized to include the addition of a crosslinkable functional group. The addition of the crosslinkable functional group to the polymers can be performed using any method or techniques known in the art, for example the methods reported in Wang, S. et al., Biomaterials, 27, pp. 832-841 (2006), which is incorporated in its entirety by reference. Biodegradable polymers can gradually release at least one additive from the biomaterial-based implant following implantation. The release rate can be between about 1 ng/hr to about 1 g/hr.

The mixtures of the invention can include other components in addition to the biomaterial and crosslinkable material. Suitable additives include, but are not limited to, bioactive agents, biocompatible minerals, and combinations thereof. Between about 0 wt. % to about 50 wt. % of the additive in the total weight of the biomaterial can be used. Bioactive agents including, but not limited to, antibiotics, anti-infective agent(s) such as silver sulfadiazine, chlorhexidine, gentamicin, tobramycin, or vancomycin, or combinations thereof. The biomaterial and/or crosslinkable material can also be combined with hormones, growth factors, cells, or combinations thereof. Suitable hormones and growth factors that can be combined with the biomaterial and/or crosslinkable material include, but are not limited to, calcium regulating hormones, PHT, TGF-beta, PGE2, BMPs, IGFs and combinations thereof. Suitable cell types that can be combined with the biomaterial and/or crosslinkable material include, but are not limited to, blood cells, mesenchymal stem cells, chondroblasts, osteoblasts, and combinations thereof. Between about 0 wt. % to about 50 wt. % of hormones, growth factors, or cells can be added to the total weight of the biomaterial and/or crosslinkable material. Additionally, the biomaterial and/or crosslinkable material can be combined with biocompatible minerals including, but not limited to, bioactive glasses, calcium phosphate, calcium sulfate, hydroxyapatite, or combinations of biocompatible materials. Between about 0 wt. % to about 50 wt. % of the biocompatible minerals in the total weight of the biomaterial and/or crosslinkable material can be used.

Binding agents can include polymers, glues, gums, sugars, cellulose ethers, resins, similar materials and combinations thereof. Between about 0 wt. % to about 75 wt. % of the binding agent to the total weight of the mixture can be used with the biomaterial. Solvents can be combined with the biomaterial in the presence or absence of the binding agents to facilitate 3D printing. Between about 0 vol. % to about 90 vol. % of the solvent can be used in the total mixture. The viscosity of the mixture at about 25° C. after the solvent is added can be between about 0.70 mPa-s to about 1000 mPa-s. The solvents can include water, alcohols, biocompatible organic solvents, buffers, similar materials and combinations thereof. Suitable biocompatible organic solvents include, but are not limited to, acetonitrile, dimethyl sulfoxide, acetone, ethyl acetate and combinations thereof. Suitable alcohols include, but are not limited to, ethanol, isopropanol, methanol and combinations thereof. Suitable buffers include, but are not limited to, Hank's balanced salt solution, phosphate buffered saline, saline and combinations thereof.

Commonly, 3D printing technology utilizes heat and laser sintering which provide temperatures of a range of about 50-250° C. during the curing process. Each layer cures shortly after it is applied. It is well known in the art that elevated temperatures are damaging to a wide variety biomaterials. For example, the natural bone morphogenetic proteins (BMPs) in bone degrade at elevated temperatures (see, Ohta, H.; et al. J. Bone Miner. Metab. 23, pp. 420-425 (2005), which is incorporated by reference in its entirety). As a result bone-based implants formed by traditional 3D printing curing conditions experience reduced or eliminated native osteoinductivity. The process of utilizing mild crosslinking conditions with bone-based biomaterials as described herein allows preservation of the bone tissue's native physical integrity and retained osteoinductivity.

An aspect of the invention is a method of 3D printing a biomaterial-based implant. The method includes combining a biomaterial and a suitable crosslinking agent using a 3D printer to create an implant of desired dimensions.

Components of the 3D printer in contact with the biomaterial can be fully removable and sterilizable. A mixture of the biomaterial and the crosslinkable material can be provided in a replaceable cartridge. The replaceable cartridges can include an additive selected from the group consisting of a bioactive agent, a binding agent, a growth factor, a hormone, a cell, an antibiotic, a biocompatible mineral, and an antimicrobial or combinations thereof. The 3D printer can crosslinks the crosslinkable material and the biomaterial.

The temperature of the 3-D printer head can be kept below about 50° C., in some embodiments between about 20° C. and about 45° C. so that the biomaterial is not damaged during formation. The printer can include or be adapted to receive at least one replaceable cartridge. In some embodiments, the printer can also be capable of utilizing light or radiation to subject the materials to visible or ultraviolet light during manufacturing to crosslink the crosslinking agent. In some embodiments, the printer can be capable of withstanding oxidation conditions to crosslink the crosslinking agent in the implant. The implant can retain biological activity. Biological activity that can be preserved includes, but is not limited to, at least one of osteoconductivity, osteoinductivity, chondroinductivity, cellular recruitment, and cell differentiation. The biological activity is at least about 80% of the biological activity of a natural bone body, cartilage body, or applicable biomaterial body source. Furthermore, the biological activity can include the activity of native and intrinsic growth factors within the bone matter to promote osteoinductivity of the resultant biomaterial-based implant. Native and intrinsic growth factors that can be maximally preserved within the biomaterial-based implant include, but are not limited to, calcium regulating hormones, PHT, TGF-beta, PGE2, BMPs, and IGFs. The mild crosslinking conditions can include visible light exposure or ultraviolet light exposure or combinations thereof. Other mild crosslinking conditions can include ozone oxidation, air oxidation, oxygen-rich atmosphere exposure, and oxidation by exposure to other oxidizing gases.

In some embodiments, the implant can range in thickness from about 0.1 mm to 100 mm, from about 0.3 mm to 50 mm, from about 0.5 to 30 mm. The biomaterial-based implant can range in length from about 5 mm to 500 cm, from about 10 mm to 200 cm, from about 10 mm to 100 cm. The biomaterial-based implant can range in width from about 5 mm to 50 cm, from about 10 mm to 20 cm, from about 10 mm to 10 cm. Each layer of the 3D biomaterial-based implant can range from about 0.01 mm to about 1.0 mm. In some embodiments, between about 1 to about 50,000 layers of the biomaterial can be layered to produce the 3D biomaterial-based implant. At least one dimension can be determined by at least one dimension of an implantation site.

The biomaterial of the implant can be selected from the group consisting of a bone, a connective tissue, a tendon, a pericardium, a dermis, a cornea, a dura matter, a fascia, a heart valve, a ligament, a capsular graft, a cartilage, a collagen, a nerve, a placental tissue, and combinations thereof. When the biomaterial is bone, the bone can be cortical bone, cancellous bone, corticocancellous bone, or combinations thereof. The bone can be demineralized, partially demineralized, fully mineralized, or combinations thereof. In some embodiments, the biomaterial-based implants can be formed from DBM with a residual calcium level of less than or equal to about 8%, about 6%, about 4%, or about 2%. In some embodiments, the residual calcium level can be about 0%.

The biomaterial can be combined with a crosslinkable material, an additive, a binder, a solvent, or combinations thereof. Suitable crosslinkable materials include, but are not limited to, a biodegradable polymer, a biocompatible polymer, and combinations thereof. The polymers or copolymers which can be used for this invention specifically relate to biodegradable polymers. Biodegradable polymers or copolymers which can be used for this invention include, but are not limited to, polycaprolactones, polyethylene glycols, polyhydroxyalkanoates, polyesteramides, polylactides, polyglycolides, poly(lactide-co-glycolide)s, polyorthoesters, polyoxazolines, and polyurethanes. These polymers can be used alone or in combination with one another. In preferred embodiments, the polymers can be derivatized to include the addition of a crosslinkable functional group. The addition of the crosslinkable functional group to the polymers can be performed using any method or techniques known in the art, for example the methods reported in Wang, S. et al., Biomaterials, 27, pp. 832-841 (2006), which is incorporated in its entirety by reference. Biodegradable polymers can gradually release at least one additive from the biomaterial-based implant following implantation. The release rate can be between about 1 ng/hr to about 1 g/hr.

The 3D printable mixtures of the invention can include other components in addition to the biomaterial and crosslinkable material. Suitable additives include, but are not limited to, bioactive agents, biocompatible minerals, and combinations thereof. Between about 0 wt. % to about 50 wt. % of the additive in the total weight of the biomaterial can be used. Bioactive agents including, but not limited to, antibiotics, anti-infective agent(s) such as silver sulfadiazine, chlorhexidine, gentamicin, tobramycin, or vancomycin, or combinations thereof. The biomaterial and/or crosslinkable material can also be combined with hormones, growth factors, cells, or combinations thereof. Suitable hormones and growth factors that can be combined with the biomaterial and/or crosslinkable material include, but are not limited to, calcium regulating hormones, PHT, TGF-beta, PGE2, BMPs, IGFs and combinations thereof. Suitable cell types that can be combined with the biomaterial and/or crosslinkable material include, but are not limited to, blood cells, mesenchymal stem cells, chondroblasts, osteoblasts, and combinations thereof. Between about 0 wt. % to about 50 wt. % of hormones, growth factors, or cells can be added to the total weight of the biomaterial and/or crosslinkable material. Additionally, the biomaterial and/or crosslinkable material can be combined with biocompatible minerals including, but not limited to, bioactive glasses, calcium phosphate, calcium sulfate, hydroxyapatite, or combinations of biocompatible materials. Between about 0 wt. % to about 50 wt. % of the biocompatible minerals in the total weight of the biomaterial and/or crosslinkable material can be used.

Binding agents can include polymers, glues, gums, sugars, cellulose ethers, resins, similar materials and combinations thereof. Between about 0 wt. % to about 75 wt. % of the binding agent to the total weight of the mixture can be used with the biomaterial. Solvents can be combined with the biomaterial in the presence or absence of the binding agents to facilitate 3D printing. Between about 0 vol. % to about 90 vol. % of the solvent can be used in the total mixture. The viscosity of the mixture at about 25° C. after the solvent is added can be between about 0.70 mPa-s to about 1000 mPa-s. The solvents can include water, alcohols, biocompatible organic solvents, buffers, similar materials and combinations thereof. Suitable biocompatible organic solvents include, but are not limited to, acetonitrile, dimethyl sulfoxide, acetone, ethyl acetate and combinations thereof. Suitable alcohols include, but are not limited to, ethanol, isopropanol, methanol and combinations thereof. Suitable buffers include, but are not limited to, Hank's balanced salt solution, phosphate buffered saline, saline and combinations thereof.

In additional embodiments, the 3D printed polymer/biomaterial mixture can be printed around a structural implant to allow use of the technology to provide implants with structural support capabilities, bioactive agents, biocompatible minerals, or combinations thereof. Suitable interior structural implants include, but are not limited to, cortical bone, cancellous bone, corticocancellous bone, 316LV stainless steel, Grade V titanium, PEEK, or other suitable rigid materials, and combinations thereof.

FIG. 1 illustrates a method of forming biomaterial-based implant 1. Step 1 illustrates visualization 2 of an implantation site in or on a patient's body. The patient can be an animal, and preferably a human. An implantation site can be visualized by imaging, drawing, or modeling. Medical imaging techniques include x-ray fluoroscopy, magnetic resonance imaging, CT scanning, and ultrasound imaging. In some embodiments, the visualization of the implantation site, Step 1, can be omitted. In embodiments without a visualization step, the dimensions of the implant can be selected from a pool of various implant sizes. Implant sizes can vary based on the common sizes required for a particular implantation. For example, an implant of the dimensions about 50 mm×about 5 mm×about 5 mm can be selected for implantation. If the implant dimensions are slightly oversized, the implant can be reduced in size by trimming, compression, or other treatment by the end user. Alternatively, if an implant of a specific size is selected and found to be too small for the implantation site, another implant of suitable size can be used in addition to the first implant selected.

Following visualization 2 of the implantation site, the desired dimensions of the implant can be selected to fit the visualized implantation site and entered into a computer-aided design (CAD) software program. Optionally, the visualization step of the method can be omitted, and the desired implant dimensions can be entered into a CAD software program. Once the desired implant dimensions are entered into a CAD software program, the 3D printing can take place on a movable platform 4 (which can be moved up or down as illustrated in FIG. 1 as 3). Above the platform 4, a movable extrusion head 6 (which can move in at least two dimensions, illustrated in FIG. 1 as 5) can deliver the semi-solid 7 biomaterial mixture to be shaped and crosslinked 8 on the platform 4 stepwise each layer of the biomaterial mixture 10 is printed. The printing speed can range from about 1 to about 100 seconds per layer. The biomaterial 9 can be prepared into a mixture 10 with a crosslinkable material, which can be fed into the extrusion head during the 3D printing. Alternatively, the biomaterial 9 and crosslinkable materials can be fed into the extrusion head via multiple supply feeds to generate the mixture 10 concurrent to the 3-D printing process. The biomaterial can be in morselized, powdered, fibrous, or in another particulate form. Binding agents can be combined with the biomaterial 9 into the mixture 10 to provide a biomaterial-based implant of the desired physical properties and cohesiveness.

EXAMPLES

Example 1

Clinical Applications for Crosslinkable Biomaterial-Based Implants

The following examples are clinical applications and uses for the articles of the present invention.

Use as a Highly Cohesive Biomaterial-Based Putty: A bioresorbable, and biocompatible putty can be formed by combining biomaterial material (such as bone or cartilage) with a crosslinkable material (e.g., UV curable). The mixture of biomaterial and crosslinkable material can be combined with other additives, growth factors, binders or combination thereof to tailor the putty to the desired physical characteristics. This mixture putty material would then allow intra-operative curing of the putty pre- or post-implantation within a patient (via various crosslinking methods, such as atmospheric oxidation or UV exposure). This provides additional putty cohesion to allow aggressive implantation site irrigation with putty migration.

Use as Osteoconductive, Osteoinductive Scaffolding: Porous blocks of bone-based materials can be formed via the 3D printing method of the present invention with retained osteoinductivity. These blocks can be formed into unique shapes, sizes, with selected porosity and densities. These custom scaffolding blocks can be used to supplement the bone void filling sizes and shapes available from other osteoinductive, bone-based materials.

Use in Small Joint Replacement: Bone material can be combined with a crosslinkable material to be 3D printed into the exact, desired shape of a unique patient's bone joint requiring replacement. Once the bone center of the joint replacement is 3D printed, a layer of cartilage-based biomaterial combined with a crosslinkable material can be printed on the surface of the bone center. Following implantation as a joint replacement, the secondary artificial chondral interface provides lowered friction between the surface of the implant and the patient's contacting articulating surfaces. Applications of this technology can be applied to arthritic, gout affected, joint deformities, joint injuries, or other joint replacement applications.

Use with Weight-Bearing, Structural Implants: Biomaterial can be combined with a crosslinkable material to be printed unto the surface of structural implants. Structural implants can be made out of implantation grade materials such as Grade V titanium, 316LV stainless steel. The printing of the mixture onto the surface of structural implants allows the use of the article in large and weight-bearing applications to facilitate integration of the implant into the patient's native tissues.

Example 2

Preparation of 3D Printed, Crosslinked Bone-Based Implants

A section of human cortical bone was ground into powder of about 212-850 µm diameter. The bone powder was then demineralized following a modified version of the demineralization steps described in U.S. Pat. No. 5,314,476, which is incorporated in its entirety by reference. Briefly, the powder was stirred in 0.6 N HCl (about 15 mL/g of bone). The acid mixture was stirred for two hours at about room temperature. Following decanting of the acid, the powder was covered and rinsed two times with water. The water for each rinse was replaced at about ten-minute intervals. Following decanting of the final water rinse, the demineralized bone powder was covered with about 0.1 M sodium phosphate and soaked at about room temperature until the pH of the solution was greater than about 6.8.

Poly(caprolactone fumarate) (PCLF) was prepared as described in Wang, S. et al., Biomaterials, 27, pp. 832-841 (2006). The PCLF (about 9.0 g) was combined with phenylbis(2,4,6-trimethylbenzoyl)-phosphine oxide (BAPO) (about 0.45 g), anisole (about 1.5 mL), and the demineralized bone powder (about 1.0 g). The mixture was vortexed until completely homogenous.

Figure 2:
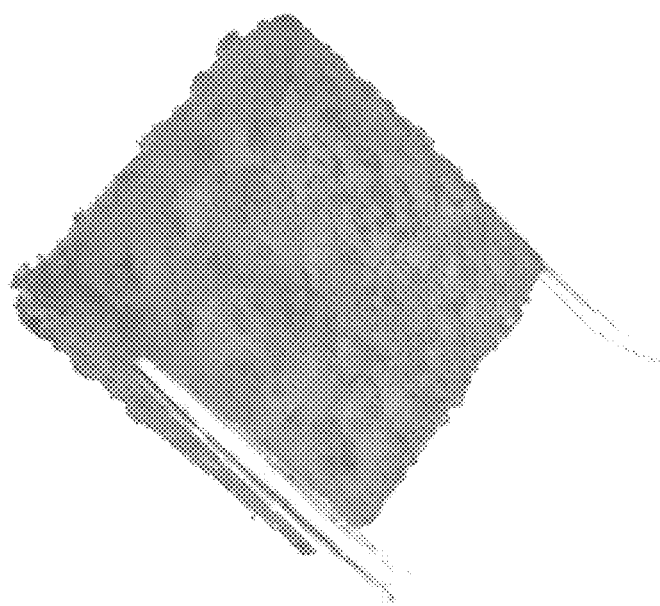
FIG. 2 illustrates a 3D printed, crosslinked bone-based implant produced by an exemplary embodiments of the disclosed method (with coloring inverted in image).

The mixture was then printed with a modified mUVe 1 Direct Light Processing (DLP) printer. With a layer height of 0.1 mm per layer, the cure time was set at 60,000 milliseconds for the first two bottom layers and set to 45,000 milliseconds for the remaining layers. The printed composite bone block was 15 mm×15 mm×4 mm, illustrated in FIG. 2. After 3D printing, the samples were terminally sterilized by gamma irradiation.

Example 3

Osteoinductivity of 3D Printed, Crosslinked Bone-Based Implants

To assess the biocompatibility and osteoinductivity of the 3D printed implants, the sample prepared as described in Example 2 was evaluated for osteinductive potential using a standardized athymic nude rat model [Edwards J T et al., Clinical Orthopedics and Related Research, 357, pp. 219-228 (1998)]. The 3D printed implant was implanted into a nude athymic rat for a 28-day implant period. Two intramuscular implant sites in the biceps femoris muscles were used. In the course of the study, no abnormal clinical signs were noted. Elements of new bone formation were observed in each of the implant sites. As the samples met the histological criteria for evidence of osteoinduction, the material demonstrated osteinduction potential in the in vivo assay.

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed:

1. A biomaterial-based implant formed under a mild crosslinking condition wherein the mild crosslinking condition is selected from the group consisting of a visible light exposure, an ultraviolet exposure and combinations thereof, wherein at least one pre-implantation property selected from the group consisting of a cohesion, a shape, and a size of the biomaterial-based implants is within between about 60% to about 100% of the at least one preimplantation property for up to about five years following formation of the implant and wherein the biomaterial-based implant retains greater than 80% of at least one biological activity selected from the group consisting of an osteoconductivity, an osteoinductivity, a chondroinductivity, a cellular recruitment, and a cell differentiation, and wherein the biomaterial-based implant comprises between two layers and about 50,000 layers of the biomaterial, wherein the biomaterial comprises a bone and a polymer, wherein the polymer is a biocompatible polymer, a biodegradable polymer or a combination thereof.

2. The implant of claim 1, wherein the biomaterial-based implant ranges in thickness from about 0.1 mm to 100 mm, ranges in length from about 5 mm to 50 cm, and ranges in width from about 5 mm to 50 cm.

3. The implant of claim 1, wherein the biomaterial of the implant further comprises a material selected from the group consisting of a connective tissue, a tendon, a pericardium, a dermis, a cornea, a dura matter, a fascia, a heart valve, a ligament, a capsular graft, a cartilage, a collagen, a nerve, a placental tissue, and combinations thereof.

4. The implant of claim 1, wherein the bone is at least one of a cortical bone, a cancellous bone, or a corticocancellous bone.

5. The implant of claim 1, wherein the bone is at least one of a demineralized bone, a partially demineralized bone, or a fully mineralized bone.

6. The implant of claim 1, wherein the biomaterial is combined with at least one of a crosslinkable material, an additive, a binder, and a solvent.

7. The implant of claim 1, wherein the polymer is the biodegradable polymer and wherein the biodegradable polymer is selected from the group consisting of a crosslinkable polycaprolactones, a polyethylene glycols, a polyhydroxyalkanoates, a polyesteramides, a polylactides, a polyglycolides, a poly(lactide-co-glycolide)s, a polyorthoesters, a polyoxazolines, a polyurethanes, combinations, and crosslinkable derivatives thereof.

8. The implant of claim 1, wherein the polymer is a biodegradable polymer and provides gradual release of at least one additive from the biomaterial-based implant following implantation.

9. A three-dimensional printed biomaterial-based implant formed under a mild crosslinking condition wherein the mild crosslinking condition is selected from the group consisting of a visible light exposure, an ultraviolet exposure and combinations thereof, and wherein the three-dimensional printed biomaterial-based implant is produced with a three-dimensional printer, comprising:
 a biomaterial comprises a bone and further comprises at least one of a connective tissue, a tendon, a pericardium, a dermis, a cornea, a dura matter, a fascia, a heart valve, a ligament, a capsular graft, a cartilage, a collagen, a nerve, and a placental tissue;
 a crosslinking material, wherein the crosslinkable material is selected from the group consisting of a biodegradable polymer, a biocompatible polymer, and combinations thereof;
 a thickness of between about 0.1 mm to 100 mm;
 a length of between about 5 mm to 50 cm;
 a width of between about 5 mm to 50 cm;
 at least 80% of at least one biological activity selected from the group consisting of an osteoconductivity, an osteoinductivity, an chondroinductivity, a cellular recruitment, and a cell differentiation; and
 between 60% to about 100% of at least one pre-implantation property selected from the group consisting of a cohesion, a shape, and a size of the biomaterial-based implants, wherein the at least one preimplantation property is maintained for up to about five years following formation of the implant, and wherein the biomaterial-based implant comprises between two layers and about 50,000 layers of the biomaterial.

10. The implant of claim 9, further comprising at least one of a native growth factor or an intrinsic growth factor.

11. The implant of claim 9, wherein the bone is selected from the group consisting of a cortical bone, a cancellous bone, and a corticocancellous bone.

12. The implant of claim 9, wherein the bone is a demineralized bone, a partially demineralized bone, a fully mineralized bone, or combinations thereof.

13. The implant of claim 9, wherein the bone is at least partially demineralized and wherein a residual calcium content of the bone is less than or equal to about 8%.

14. The implant of claim 9, wherein the crosslinking material is the biodegradable polymer selected from the group consisting of a polycaprolactone, a polyethylene glycol, a polyhydroxyalkanoate, a polyesteramide, a polylactide, a polyglycolide, a poly(lactide-co-glycolide), a polyorthoester, a polyoxazoline, a polyurethane, and copolymers thereof.

15. The implant of claim 9, further comprising an additive, a binder, a solvent, or combinations thereof.

16. The implant of claim 9, further comprising between about 0 wt. % to about 50 wt. % of an additive in the total weight of the biomaterial, wherein the additive is selected from the group consisting of a bioactive agent, a biocompatible mineral, and combinations thereof.

17. The implant of claim 16, wherein the additive is the bioactive agent and selected from the group consisting of an antibiotic, an anti-infective agent, and combinations thereof.

18. The implant of claim 17, wherein the bioactive agent is the anti-infective agent and is selected from the group consisting of a silver sulfadiazine, a chlorhexidine, a gentamicin, a tobramycin, a vancomycin, and combinations thereof.

19. The implant of claim 9, further comprising at least one of a hormone, a growth factor, or a cell.

20. The implant of claim 9, further comprising up to about 75 wt. % of a binding agent.

21. A three-dimensional printed biomaterial-based implant, comprising:
   a biomaterial comprises a bone and further comprises at least one of a connective tissue, a tendon, a pericardium, a dermis, a cornea, a dura matter, a fascia, a heart valve, a ligament, a capsular graft, a cartilage, a collagen, a nerve, a placental tissue, and combinations thereof;
   a crosslinking material, wherein the crosslinkable material is selected from the group consisting of a biodegradable polymer, a biocompatible polymer, and combinations thereof;
   at least one of an additive, a hormone, or a binder; and
   at least one of a native growth factor or an intrinsic growth factor;
   wherein a thickness of the implant is between about 0.1 mm to 100 mm;
   wherein a length of the implant is between about 5 mm to 50 cm;
   wherein a width of the implant is between about 5 mm to 50 cm;
   wherein at least 80% of at least one biological activity selected from the group consisting of an osteoconductivity, an osteoinductivity, a chondroinductivity, a cellular recruitment, and a cell differentiation;
   wherein between 60% to about 100% of at least one pre-implantation property selected from the group consisting of a cohesion, a shape, and a size of the biomaterial-based implants, wherein the at least one preimplantation property is maintained for up to about five years following formation of the implant; and
   wherein the biomaterial-based implant comprises between two layers and about 50,000 layers of the biomaterial.

22. The implant of claim 21, wherein the crosslinking material is the biodegradable polymer selected from the group consisting of a polycaprolactone, a polyethylene glycol, a polyhydroxyalkanoate, a polyesteramide, a polylactide, a polyglycolide, a poly(lactide-co-glycolide), a polyorthoester, a polyoxazoline, a polyurethane, and copolymers thereof.

23. The implant of claim 21, wherein the binder is selected from the group consisting of a binder polymer, a glue, a gum, a sugar, a cellulose ether, a resin and combinations thereof.

* * * * *